(12) United States Patent
Sholev

(10) Patent No.: US 12,364,573 B1
(45) Date of Patent: Jul. 22, 2025

(54) SURGICAL PORT WITH INTEGRATED CLEANING MEANS

(71) Applicant: SCOPIX LTD., Amikam (IL)

(72) Inventor: Mordehai Sholev, Amikam (IL)

(73) Assignee: SCOPIX LTD., Amikam (IL)

( * ) Notice: Subject to any disclaimer, the term of this patent is extended or adjusted under 35 U.S.C. 154(b) by 0 days.

(21) Appl. No.: 18/914,330

(22) Filed: Oct. 14, 2024

(51) Int. Cl.
 *A61B 90/70* (2016.01)
 *A61B 17/34* (2006.01)
 *A61B 17/00* (2006.01)

(52) U.S. Cl.
 CPC .......... *A61B 90/70* (2016.02); *A61B 17/3423* (2013.01); *A61B 2017/00862* (2013.01)

(58) Field of Classification Search
 CPC ................ A61B 90/70; A61B 17/3423; A61B 2017/00862
 See application file for complete search history.

(56) References Cited

U.S. PATENT DOCUMENTS

| | | | |
|---|---|---|---|
| 6,354,992 B1 | 3/2002 | Kato | |
| 8,047,215 B1 | 11/2011 | Sasaki | |
| 8,535,220 B2 | 9/2013 | Mondschein | |
| 8,888,689 B2 | 11/2014 | Poll et al. | |
| 8,945,155 B2 | 2/2015 | Gordin et al. | |
| 2009/0240111 A1 | 9/2009 | Kessler et al. | |
| 2014/0318582 A1 | 10/2014 | Mowlai-Ashtiani | |
| 2015/0080660 A1 | 3/2015 | Gomez et al. | |
| 2020/0060536 A1* | 2/2020 | Rylander | A61B 1/00135 |

* cited by examiner

*Primary Examiner* — Richard G Louis

(74) *Attorney, Agent, or Firm* — The Roy Gross Law Firm, LLC; Roy D. Gross

(57) ABSTRACT

The present invention discloses a surgical port integrated with cleaning means, and methods thereof for cleaning the lens and light source of an endoscope.

20 Claims, 15 Drawing Sheets

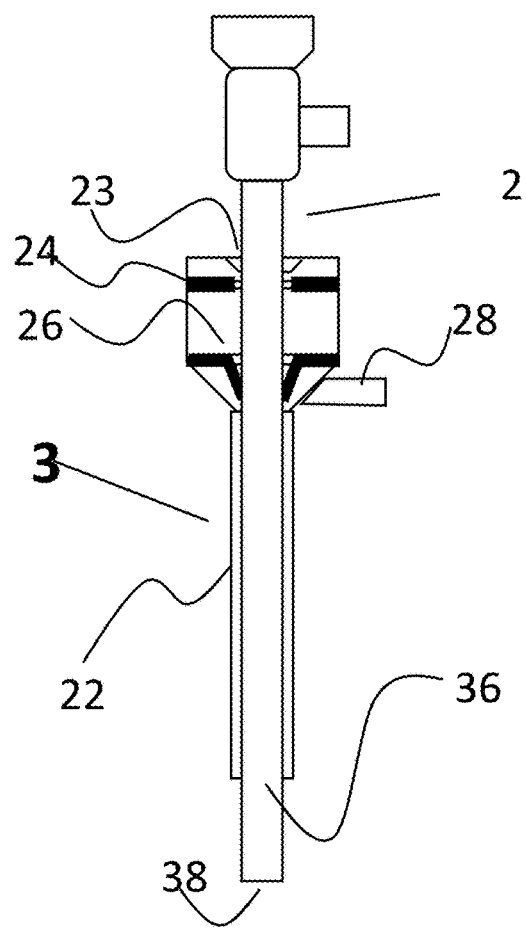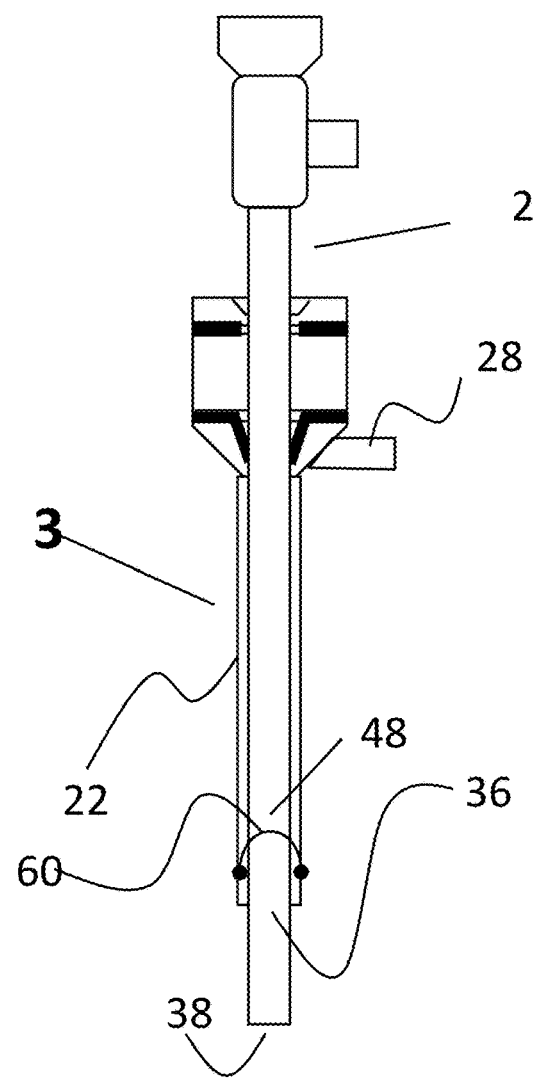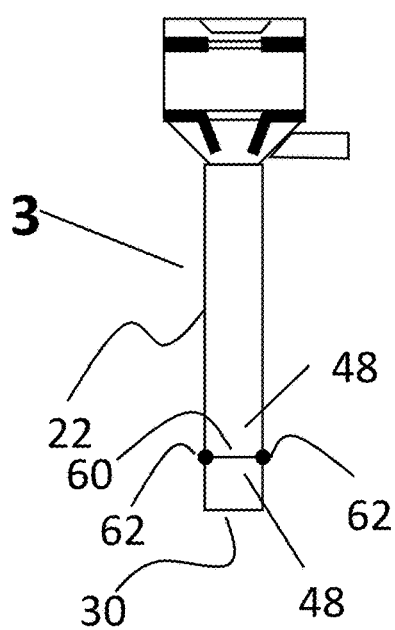
Figure 3
Figure 4B
Figure 4A

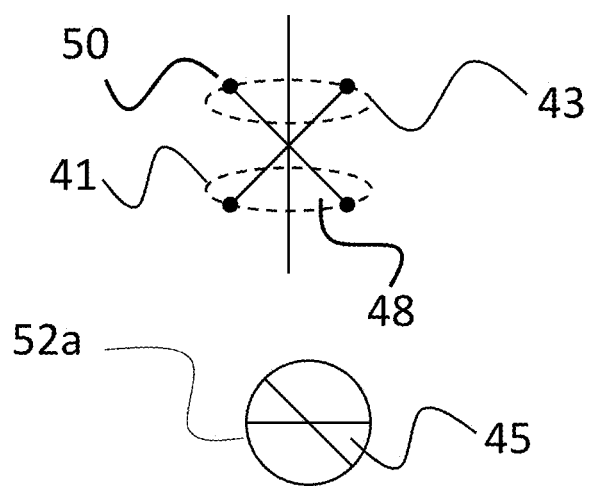
Figure 6E
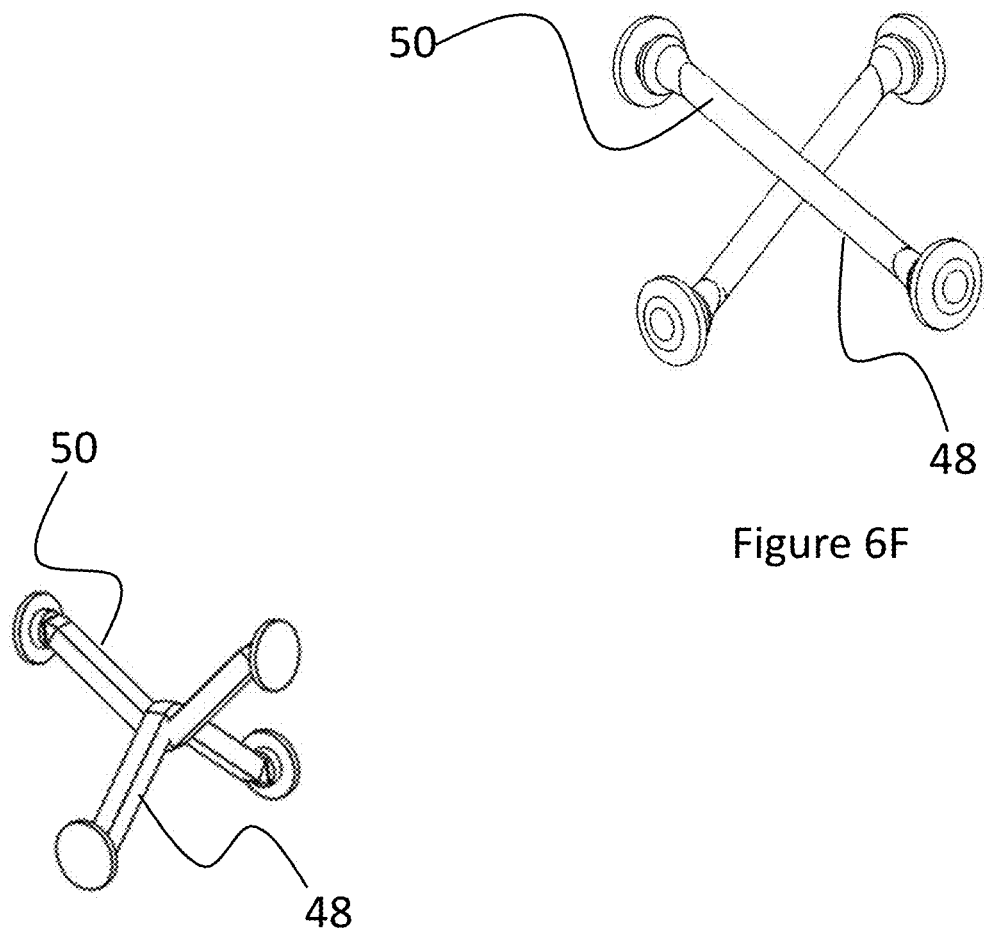
Figure 6F
Figure 6G

SURGICAL PORT WITH INTEGRATED CLEANING MEANS

FIELD AND BACKGROUND OF THE INVENTION

A minimally invasive procedure causes less operative trauma, fewer post-operative complications, and fewer adverse effects compared to an equivalent open surgery. For example, laparoscopic surgery reduces post-operative discomfort and speeds up healing, while also decreasing hospitalization time and associated costs.

Minimally invasive surgeons use instruments that can be operated externally to manipulate tissues within the body. To accurately guide these tools and perform the procedure, they rely on an endoscope, which provides a visual of the tools and the target tissues inside the body. Some procedures, such as diagnostic ones, may be performed solely with an endoscope.

Fouling of an endoscope's objective lens is a common issue during minimally invasive surgeries, reducing the field of view and image quality. This requires the surgeon to repeatedly remove and clean the lens, prolonging the procedure and increasing infection risks. Various solutions have been suggested, including cleaning sheaths, heating methods, and anti-fog treatments as outlined in patents such as U.S. Pat. Nos. 6,354,992, 8,047,215, 8,535,220, 8,888,689, 8,945,155, US20090240111, US20140318582, US20150080660, and US20200060536. However, there remains a need for a simple, cost-effective, and efficient solution to address endoscopic lens fouling.

SUMMARY OF THE INVENTION

The present invention generally relates to a surgical port and methods thereof for producing and using a surgical port adapted for cleaning endoscope lens operable in a body cavity. Embodiments of the present invention relate to a cleaning string or a system of strings attached to the cannula of the surgical port, and methods thereof for use of the same for cleaning the lens and light source of an endoscope.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

It is hence an object of the present invention to disclose a surgical port for cleaning accommodated surgical instruments comprising a cannula and an at least one elastomeric band installed in the cannula, configured to clean the surgical instruments accommodated within.

In some embodiments, the at least one elastomeric band is placed vertically to a longitudinal axis along a cannula interior body.

In some embodiments, at least two elastomeric bands are placed vertically to a longitudinal axis along a cannula interior body.

In some embodiments, at least two elastomeric bands are placed in a same plane.

In some embodiments, at least two elastomeric bands are placed on different planes.

In some embodiments, the at least one elastomeric band ends are placed on different planes.

In some embodiments, each end of each elastomeric band end is placed on different planes.

In some embodiments, at least two of the at least one elastomeric band cross one another.

In some embodiments, at least two of the at least one elastomeric band are arranged in a 3D grate pattern, a crossing pattern, or any combination thereof.

In some embodiments, the at least one elastomeric band is immobilized to the cannula.

In some embodiments, the at least one elastomeric band is made of rubber or silicone.

In some embodiments, the surgical port further comprising holes to accommodate the at least one elastomeric band.

In some embodiments, the holes are surrounded by grooves configured to protect the at least one elastomeric band.

In some embodiments, the surgical port is configured to fit either a typical obturator or a modified obturator.

In some embodiments, the modified obturator comprises head, shaft, a pointed head 72 and a modified body having a socket, the modified obturator is configured to enable the at least one elastomeric band to surround the obturator body.

In is hence another object of the present invention to disclose a method for cleaning surgical instruments within a body cavity comprising obtaining a surgical port having an at least one elastomeric band vertically to a longitudinal axis along a cannula interior body; and moving the surgical instrument over the at least one elastomeric band thereby obtaining a cleaned surgical instrument.

In some embodiments, at least two of the at least one elastomeric band cross one another.

In some embodiments, at least two of the at least one elastomeric band are arranged in a grate pattern, a crossing pattern, or any combination thereof.

In some embodiments, the at least one elastomeric band is made of rubber or silicone.

In some embodiments, the surgical port comprises a cannula having holes configured to accommodate the at least one elastomeric band.

In some embodiments, the holes are surrounded by grooves configured to protect the at least one elastomeric band.

In some embodiments, the surgical port is either obtained by modifying a standard trocar or by purchasing the surgical port.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 3 an image presenting an endoscope installed in a surgical port.

FIGS. 4A-4C are images representing (4A) a surgical port comprising one elastomeric band acting as the cleaning cord, (4B) an endoscope installed with a surgical port, and (4C) a cleaning cord according to some embodiments of the present invention.

FIGS. 6A-6G are images illustrating (6A-6C) various patterns, spatial arrangements of an at least one elastomeric band along the cannula of a surgical port, according to some embodiments of the present invention; (6D-6E) illustrating schematically planes and intersection between cleaning bands of the same pair, and (6F-6G) illustrating intersection between cleaning bands of the same pair.

DESCRIPTION OF THE PREFERRED EMBODIMENTS

While reducing the present invention to practice, the present invention comprises an at least one wiping element constructed from an at least one elastic band positioned along a lumen of the surgical port cannula. As is further described hereinbelow, the wipers assembly system can be fitted to the surgical port by holes located along its length of the cannula of the surgical port.

Before detailing at least one embodiment of the invention, it should be understood that the invention is not confined to the specific details described or illustrated in the examples. The invention can take on other forms and be implemented in different ways. Additionally, the language used here is for descriptive purposes and should not be considered limiting.

The present invention discloses a surgical port and a method for cleaning a surgical instrument, by integrating the cleaning elements within a cannula of the surgical port. The principles and operation of the present invention may be better understood with reference to the drawings and accompanying descriptions As used herein the term "surgical port" refers to any device that can be used to provide surgical access to a body cavity through a tissue surrounding the body cavity.

Figure 1:
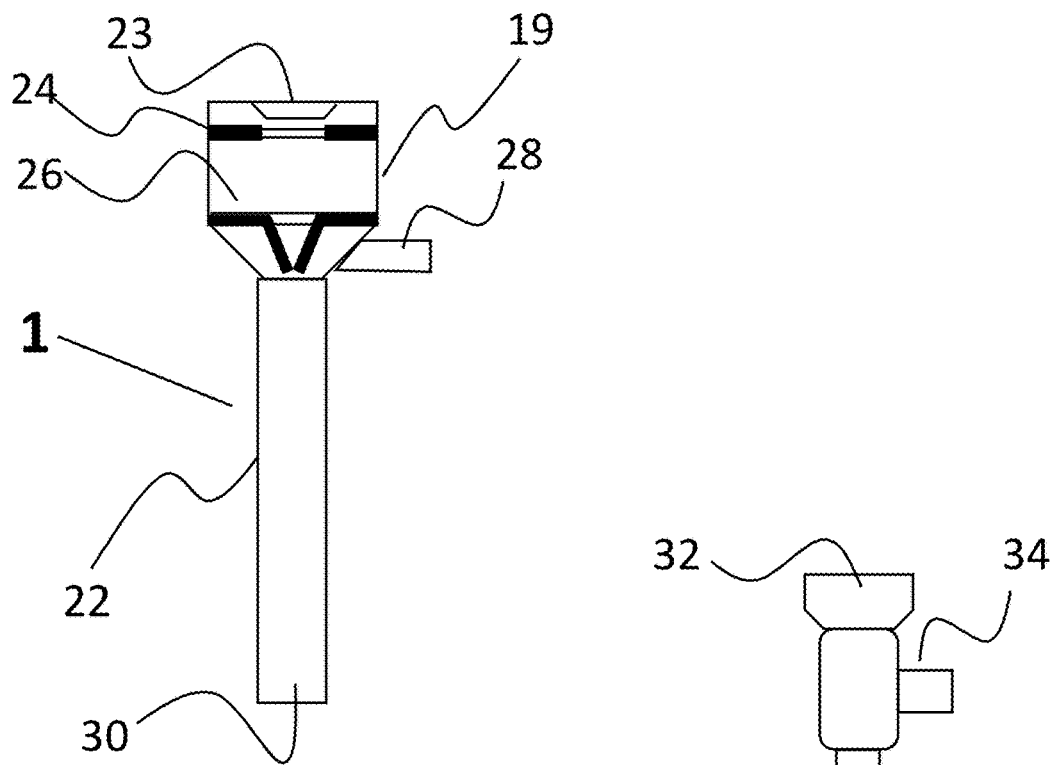
FIG. 1 is an image representing the structure of a typical surgical port.

A typical surgical port comprises cannula, a seal and optionally an awl/obturator (for piercing tissue). Surgical ports (trocars) are placed through the abdomen of the patient, during laparoscopic surgery and function as a portal for the subsequent placement of surgical instruments such as an endoscope. Reference is now made to FIG. 1 illustrating a typical surgical port 1 having a proximal cap or housing 19, a cannula 22, and a hose 28. Hose 28 is designed to deliver gas, typically carbon dioxide ($CO_2$), through cannula 22 into to the procedure site for inflation. Proximal cap 19 houses the proximal opening 23 of the surgical port 1 and typically includes an O-ring valve 24, which prevents the gas used to inflate the procedure site cavities from leaking while the endoscope is installed in surgical port 3. An additional valve 26, typically a duckbill valve, is positioned at the proximal opening of cannula 22. Valve 26 is configured to prevent gas from leaking when a surgical tool is removed from the surgical port 1.

Valve 26 is located above the opening for hose 28. Hose 28 can also be used to spray saline into the main cannula 22 to rinse the lower part of valve 26 and the lumen of cannula 22, allowing for cleaning of the interior of the lumen, shaft 36 of the endoscope 2, and the elastic cleaning bands, as will be explained later.

Figure 2A:
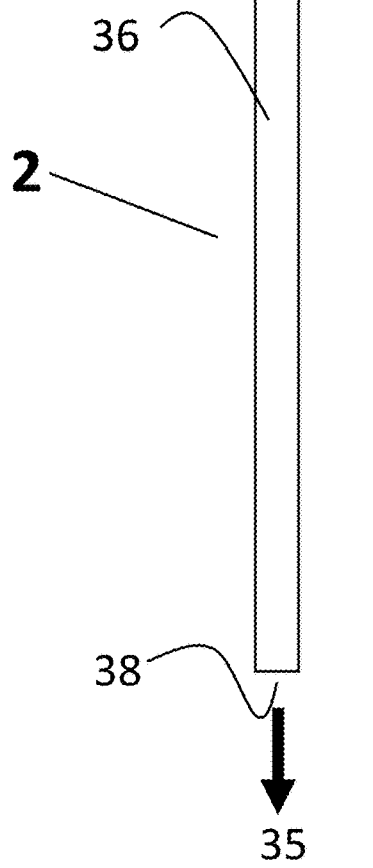
FIGS. 2A-2D are images presenting (2A-2B) typical endoscopes commonly used in minimal invasive surgical procedures with (2A) a lens positioned at a 0° angle relative to shaft and (2B) a lens positioned at a 30°/45° angle relative to shaft; and (2C-2D) common arrangement of the camera lens and the light source of a (2C) 0° angle lens and (2D) a 30°/45° angle lens.
Figure 2B:
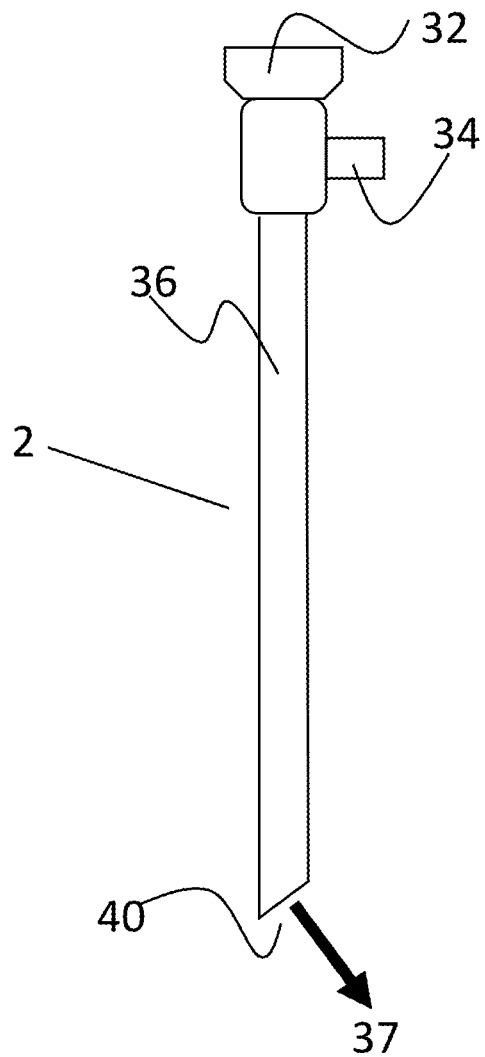

As used herein, the term "endoscope" refers to a device used for observation within a body cavity/lumen. A typical endoscope includes a rigid or flexible shaft approximately 300-500 mm in length, with an outer diameter of 3 mm to 12 mm. The shaft includes an objective lens at a distal end and an eyepiece or camera at the proximal end. The objective lens is optically coupled to the eyepiece or camera via light-transmitting glass fibers and/or rod lenses. The endoscope can also include a light source for illuminating the body cavity. FIGS. 2A-2B demonstrate a typical endoscope (2) commonly used in minimal invasive surgical procedures. Endoscope 2 features shaft 36 with a diameter ranging from 3 mm to 12 mm and a length varying between 100 mm and 500 mm. Usually, shaft 36 contains an optic fiber which connects to proximal input connector 34 and to the distal end 38/40 of shaft 36. Camera connector 32 is located at the proximal end of endoscope 2 and is configured to receive an image from a surgical site using a system of lenses located along shaft 36 to distal lens 38/40 located at the distal end of shaft 36.

In FIG. 2A endoscope lens 38 is concentric with shaft 36 (lens 38 and shaft 36 are aligned at a 0° angle). The field of view is oriented according to arrow 35. In FIG. 2B endoscope lens 40 is positioned at an angle relative to shaft 36, typically either 300 or 45°. The field of view is directed according to arrow 37.

In some embodiments, the angle of the lens at the distal end of the endoscope determines the position of the camera lens or structure of the optic fibers of the light source around the camera lens, including any combination thereof.

Figure 2C:
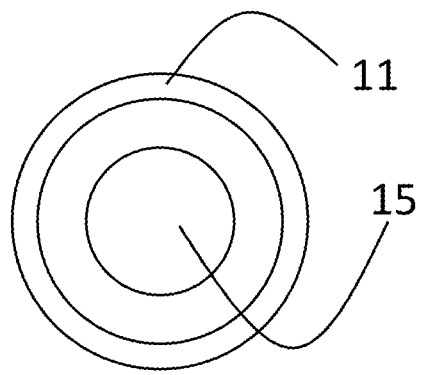

FIG. 2C illustrates common arrangement of the camera lens and the light source of an 0° angle lens. Camera lens 15 is in the center and light source 11 surrounds lens 15 in a concentric circle.

Figure 2D:
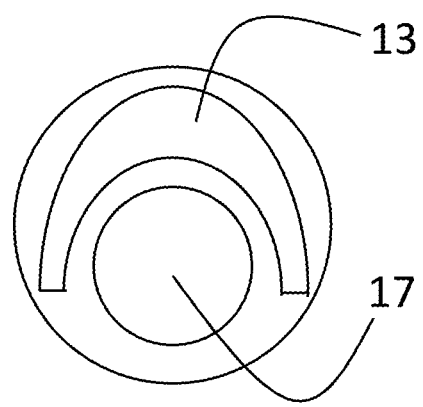

FIG. 2D illustrates common arrangement of the camera lens and the light source of a tilted lens, typically 30° or 45° angle. Camera lens 17 is located below center of shaft 36 and light source 13 is located above and in the sides of lens 17 in a concentric circle.

A person skilled in the art would appreciate that an efficient cleaning device for an endoscope lens must consider differences in structure of different type of endoscopes.

FIG. 3 demonstrates endoscope 2 installed through surgical port 3 for use in minimally invasive surgical procedures. Shaft 36 extends through proximal opening 23 located in proximal cap 19. Duckbill 26 is in an open position, while proximal O-ring 24 provides a seal around shaft 36 to prevent leakage of gas delivered through hose 28.

The surgical port according to some embodiments of the present invention comprises an at least one elastomeric band stretched across a lumen of surgical port. The elastic string is configured to wipe and clean the surface of the surgical instrument. In some embodiments, cleaning/wiping occurs while the surgical instrument is passed through the surgical port. Non-limiting examples of surgical instruments include but are not limited to endoscope, graspers, forceps, scissors, harmonic scalpel, electrocautery, suturing devices, retractors, camera and light sources, or robotic surgical instruments, including any combination thereof.

In some embodiments, the surgical instrument is an endoscope. In some embodiments, the elastomeric string is configured to clean and wipe the endoscope lens or light source, including any combination thereof. In some embodiments, cleaning and or wiping of the endoscope lens or light source the endoscope is executed by moving the endoscope through the cleaning strings system, as will be described in detail.

Reference is now made to FIG. 4A illustrates surgical port 3 comprising a single cleaning element 48. Cleaning element 48 is located near distal opening 30 of cannula 22. Cleaning element 48 is anchored to the cannula by bulges 62. The cleaning band is or comprises at least one elastomeric band 60.

As used herein, the terms "string", "cord" and "band" are used interchangeably. As used herein the terms "cleaning strings", "cleaning element" and "wiping element" refer to the same element in the invention, a flexible, elongated material which is stretched from one end of the cannula to the other and is held by bulges (62) and takes part in cleaning process of an endoscope.

FIG. 4B illustrates endoscope 2 installed through surgical port 3 according to some embodiments of the present invention. Shaft 36 extends through the distal opening of surgical port 3. The elastomeric band 60 is stretched over shaft 36 of endoscope 2, pushed to the space between shaft 36 of endoscope 2 and the sides of cannula 22 of surgical port 3.

Figure 4C:
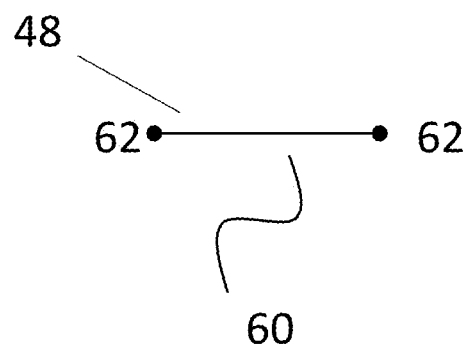

FIG. 4C demonstrates cleaning cord 48 comprising an elastomeric band 60 and two bulges 62 configured to anchor elastomeric band 60 to cannula 22 sides. In some embodiments, the elastomeric band 60 is elastomeric, and made of silicon or rubber.

Figure 5A:
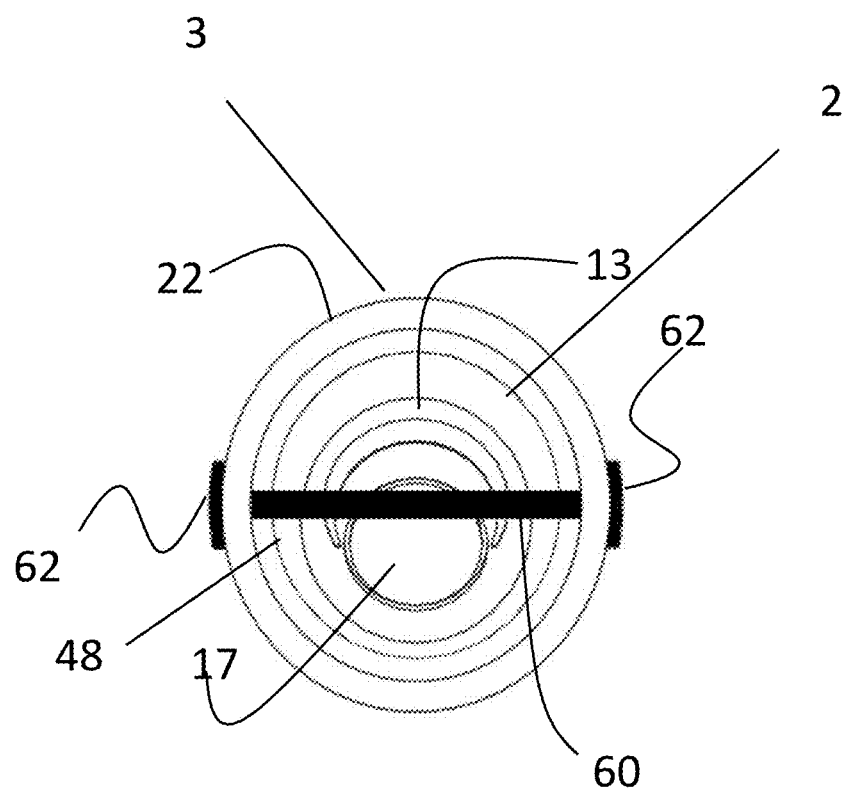
FIGS. 5A-5C are frontal view images demonstrating the use of a surgical port having at least one elastomeric band to wipe and clean an angled endoscope distal lens and light source, according to some embodiments of the invention.
Figure 5B:
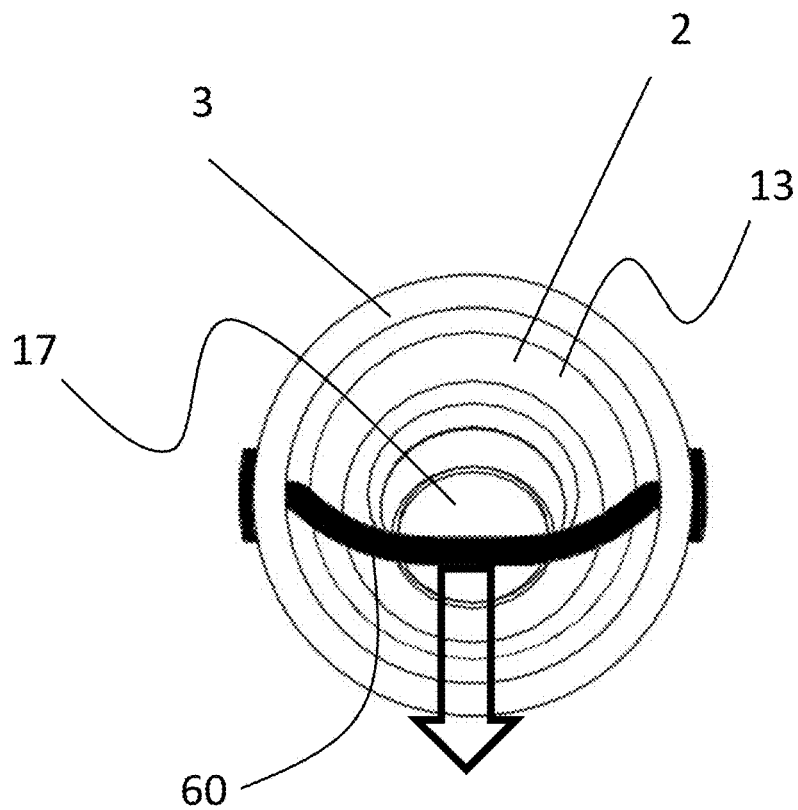
Figure 5C:
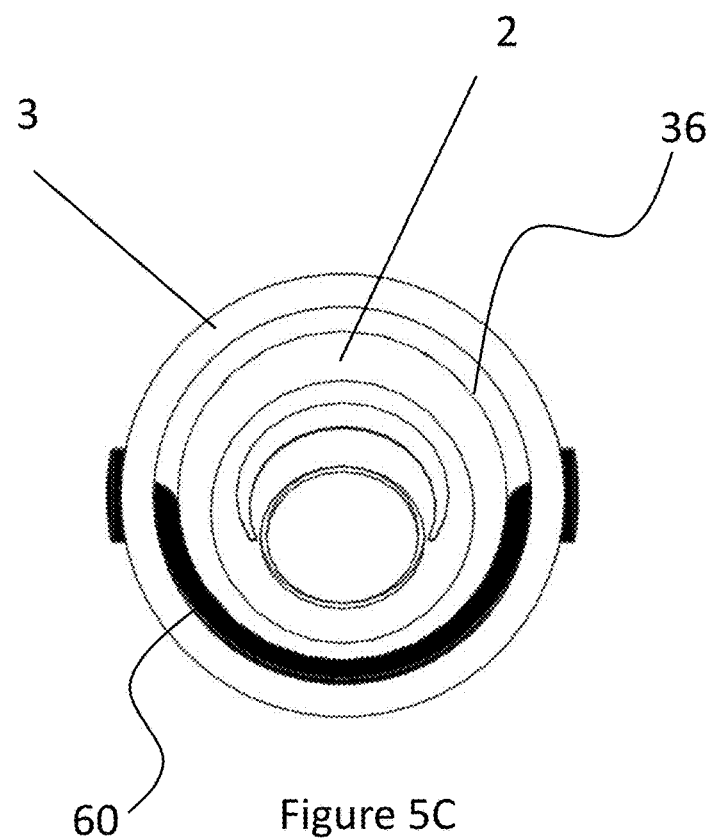

Reference is now made to FIGS. 5A-5C showing frontal views of the distal end of angled endoscope 2 installed within cannula 22 of surgical port 3, and the path of a single elastomeric band 60 over an angled endoscope distal end surface. FIG. 5A shows elastomeric band 60 at its initial position in the center of cannula 22 of surgical port 3. FIG. 5B exhibits elastomeric band 60 stretched while moving down and wiping part of camera lens 17 and part of source light 13. FIG. 5C demonstrates elastomeric cord 60 pushed under shaft 36 of endoscope 2, also shown previously in FIG. 4B, allowing the surgeon to manipulate the endoscope to a preferred position.

While the surgeon pushes endoscope 2 distal end through cannula 22, the endoscope distal end, comprising lens 17 and light source 13, must contact the elastomeric band 60 and push it away (sideways) from shaft 36 of endoscope 2. While the distal end 40 of endoscope 2 pushes elastomeric band 60, elastomeric band 60 wipes part of the distal end 40 of endoscope 2, thus may remove fog, blood, or any material from its surface, including any combination thereof. If elastomeric band 60 slides over only a portion of lens 17 or light source 13, some material might be left on the lens or light source. To clean the whole area of the distal end of the endoscope, the surgeon may pull the endoscope back to the proximal end of cannula 22, rotate the endoscope along the long axis of shaft 36, and again, push the distal end 40 of endoscope 2 against the elastomeric band 60, causing elastomeric band 60 to potentially wipe different area of the distal end 40 of the endoscope 2, depending on the position of elastomeric band 60 and the structure of the endoscope distal end flat (00 angle) or angled (300 or 450 angle).

A person skilled in the art would appreciate that a single cleaning band may not be sufficient to clean the whole surface of angled endoscope. In some embodiments, an angled endoscope requires an at least two elastomeric bands. As used herein, the term "angled endoscope" refers to an endoscope having an angled distal end.

As used herein the term "sufficient" refers to cleaning an endoscope surface by at least 80%, at least 85%, at least 87%, or at least 90%, including any value or range in between. Each possibility is a separate embodiment of the present invention.

A person skilled in the art would appreciate that while pulling the endoscope back to the proximal end of cannula 22, the elastomeric band 60 also may wipe part of the distal end of endoscope 2 due to elastic forces. In some embodiments, the elastomeric band naturally tends to retrieve its original position.

Figure 6A:
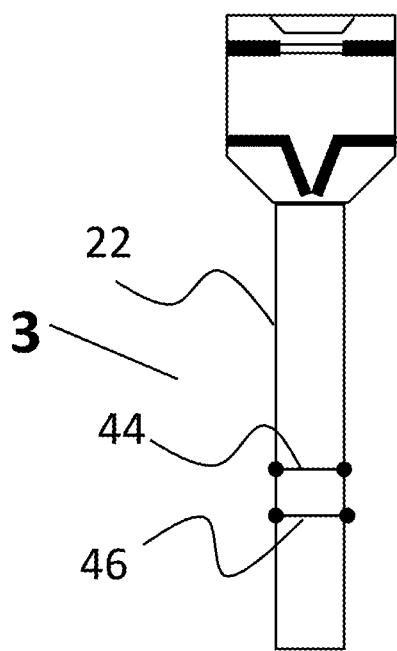

Reference is now made to FIGS. 6A-6G. FIGS. 6A-6G are illustrations of possible embodiments of cleaning bands systems positioned along the cannula 22 of a surgical port. FIG. 6A demonstrates a surgical port having two cleaning bands 44 and 46 positioned across cannula 22 of surgical port 3. Each elastomeric bands 44 and 46 are perpendicular to the longitudinal axis of cannula 22, and each cleaning band (44 and 46) is positioned in different planes 41,43, seen also in FIG. 6D, where each plane 41,43 is perpendicular to the longitudinal axis of cannula 22. Bands 44 and 46 may be at any angle 45, relative to each other as shown in top view in FIG. 6D.

As used herein, the terms "cleaning bands" and "elastomeric bands" are used interchangeably.

Figure 6B:
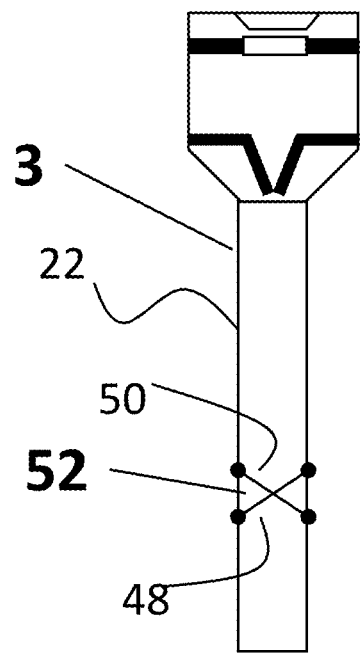

FIG. 6B illustrates a surgical port 3, according to some embodiments of the present invention, having pair of two cleaning bands 48 and 50 positioned across cannula 22 of surgical port 1, where each cleaning band 48 and 50 are positioned at an angle to the longitudinal axis of cannula 22. Cleaning bands 48 and 50 may be at any angle 45, relative to each other as shown in top view of FIG. 6E.

Figure 6C:
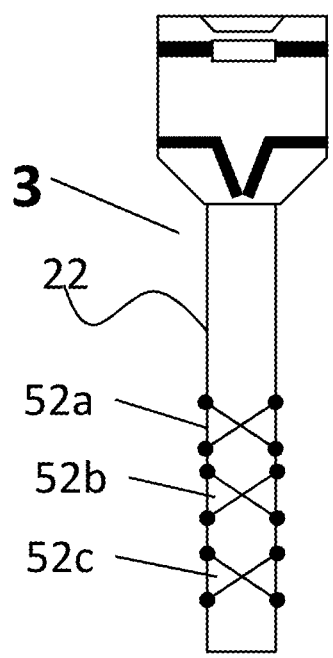
Figure 6D:
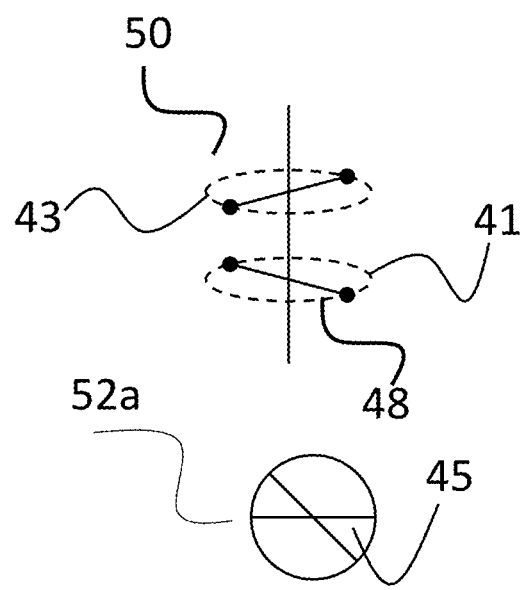

FIG. 6C illustrates a surgical port, according to some embodiments of the present invention, having three pairs of cleaning bands 52a, 52b, and 52c positioned along cannula 22 of surgical port 3. Each elastomeric band in each cleaning bands pair is positioned at an angle to the longitudinal axis of cannula 22. The elastomeric bands of each pair may be positioned in the same plane or may be positioned between different planes. Cleaning bands 48 and 50 may be at any angle 45, relative to each other as shown in FIG. 6E. A person skilled in the art would appreciate that each cleaning pair main plain may be rotated with relation to the other pairs creating spatial labyrinth of cleaning bands, as shown in FIGS. 7A-7E, allowing the wiping of the whole surface of the distal end of an endoscope.

Reference is now made to FIG. 6F-6G illustrate possible intersection between cleaning bands of the same pair, according to some embodiments of the present invention. FIG. 6F shows two cleaning bands 50 and 48, where cleaning band 50 passes over cleaning band 48. In some embodiments, the cleaning bands pairs overlap, or are spaced apart from one another, including any combination thereof. FIG. 6G demonstrates two cleaning bands 50 and 48 that cross and overlap each other. Each cleaning band causes tension on the other cleaning band. The amount of tension depends on the length of each band, the distances between the holes in cannula 22 where the cleaning band are positioned and the material properties of each band.

Figure 7A:
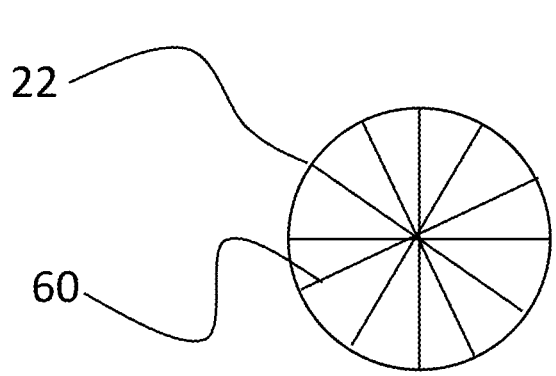
FIGS. 7A-7E illustrate various patterns, arrangements and cross-sectional shapes of an at least one elastomeric band as seen from the distal opening of the cannula of a surgical port, according to some embodiments of the invention.

Reference is now made to FIGS. 7A-7E demonstrating exemplary arrangement of plurality of elastomeric bands. FIG. 7A illustrates a radial string pattern, also shown in FIG. 9C, made of six elastomeric bands where the bands in each pair are in 90° relative angle, and each pair of bands is rotated in 120° relative to the other bands pairs. In some embodiments, the radial string pattern comprises between 3 and 10, between 3 and 9, between 3 and 8, between 3 and 7, between 3 and 6, or between 4 and 6 strings, including any value in between. Each possibility represents a separate embodiment of the present invention.

Figure 7B:
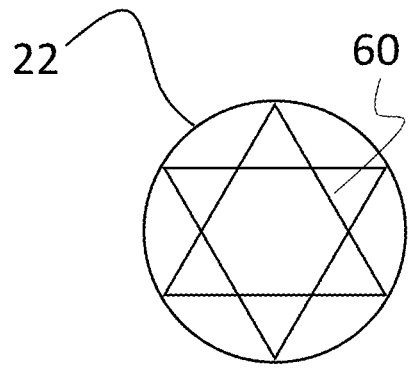

FIG. 7B presents a hexagonal star, having six elastomeric band, made of two tringles. In some embodiments, the plurality of elastomeric band is arranged in a polygonal star. In some embodiments, the polygonal star shape comprises 5, 6, 7, 8 or 10 elastomeric band and forms pentagram, hexagram, heptagram, octagram, or decagram, respectively.

Figure 7C:
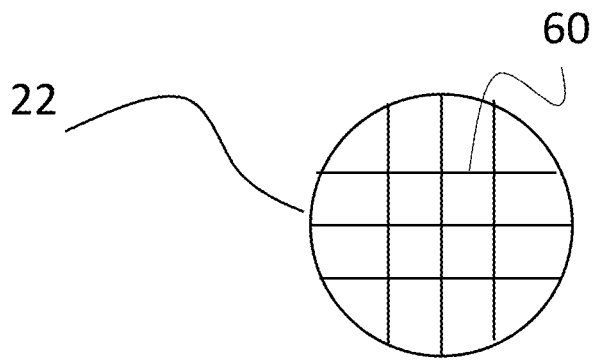

FIG. 7C shows a rectangular mess pattern made of six elastomeric bands. In some embodiments, the rectangular mess pattern comprises between 4 and 10 elastomeric bands. A person skilled in the art would appreciate that an increase in the number of elastomeric bands making the pattern increase the density of the pattern, and increases the force the surgeon has apply to the surgical instrument in order to clean it and move the endoscope shaft through the cleaning bands.

Figure 7D:
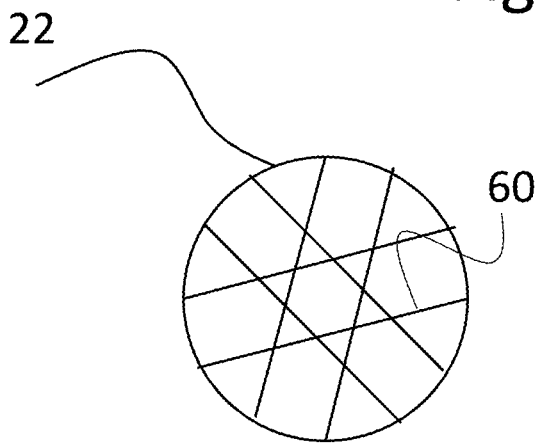

FIG. 7D presents a radially position cord pattern made of 6 elastomeric bands. In some embodiments the radially position cord pattern comprises between 4 and 10, between 4 and 8, or between 5 and 7 elastomeric bands, including any value in between. Each possibility represents a separate embodiment of the present invention.

Figure 7E:
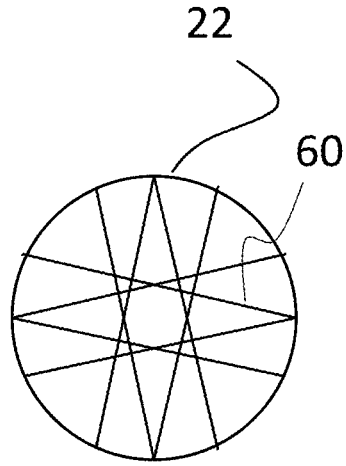

FIG. 7E demonstrates a V shape band with a meeting point at a premature disposed radially, pattern made of four V shaped bands. In some embodiments, the V shape band is formed by two elastomeric bands. A person skilled in the art would appreciate that the pattern can be made from 2, 3, 4, 5, or 6 V shaped bands, but the greater the number of V shaped bands the force the surgeon has apply to the surgical instrument in order to clean it increases.

A person skilled in the art would appreciate that in all exemplary arrangement of plurality of elastomeric bands (FIGS. 7A-7E) the elastomeric bands may overlap at least another band.

In some embodiments, the plurality of the at least one elastomeric band cross one another.

In some embodiments, the plurality of the at least one elastomeric band are arranged in a 3D grate pattern, a crossing pattern, or any combination thereof.

As used herein, the term "grate pattern" refers to a repetitive design composed of parallel lines or stripes, often resembling a grid or lattice structure. These lines typically follow a uniform direction, creating an organized and consistent visual arrangement. The grate pattern may be planner or three dimensional.

As used herein, the term "crossing pattern" refers to a pattern formed by intersecting lines or shapes that crisscross at various angles. This pattern often creates a network of connected points where lines overlap, resulting in a more complex and dynamic design compared to a single-directional pattern.

In some embodiments, the surgical port comprises an at least one elastomeric band. In some embodiments the surgical port comprises a plurality of elastomeric bands. As used herein, the term plurality refers to at least two elastomeric bands. In some embodiments, the elastomeric band is or comprises rubber or silicone, including any combination thereof. In some embodiments the elastomeric band comprise at the distal and proximal end heads 62.

In some embodiments, the surgical port of the present invention comprises at a distal end of a surgical port cannula an at least one elastomeric band configured to clean the surgical instruments accommodated within. In some embodiments, the at least one elastomeric band is immobilized or installable, including any combination thereof, at the distal end of the surgical port cannula. In some embodiments, the at least one elastomeric band is immobilized vertically to a longitudinal axis along a cannula interior body.

In some embodiments, the surgical port comprises holes along the cannula. In some embodiments, the holes are configured to hold the at least one elastomeric band from one side of the cannula interior body to the other side. In some embodiments, the at least one elastomeric band are installable within the holes. In some embodiments, the at least one installed elastomeric band are placed vertically to a longitudinal axis along a cannula interior body. In some embodiments, each elastomeric band comprises at its proximal and distal ends a head (62). In some embodiments, head 62 is configured to anchor the at least one elastomeric band within the holes along the cannula, to obtain a stretched elastomeric band from one side of the cannula to the other. In some embodiments, the stretched elastomeric band is configured to clean the surgical instrument inserted within the surgical port of the invention. In some embodiments, the stretched elastomeric band is a cleaning band.

Figure 8A:
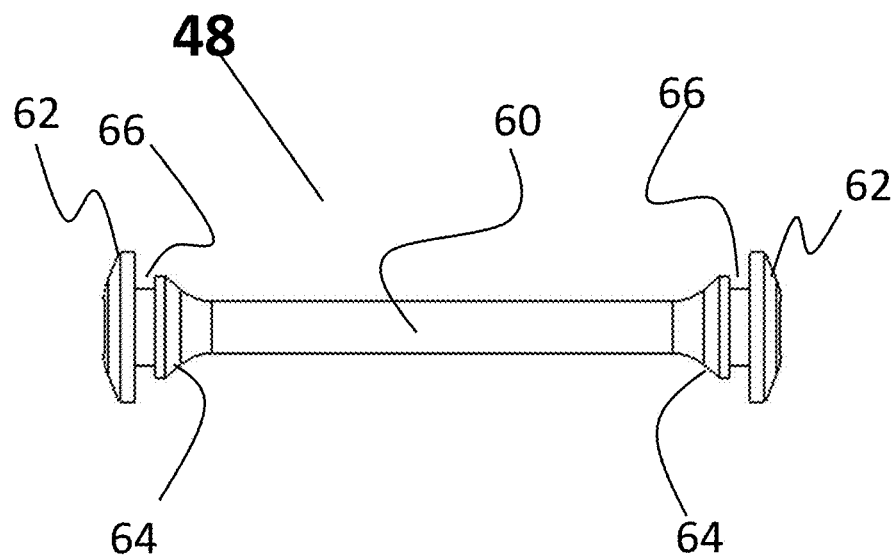
FIGS. 8A-8C are illustrations presenting (8A-8B) an elastomeric band design, and (8C) the location and structure of holes that allow the strings to be connected to the cannula, according to some embodiments of the present.
Figure 8B:
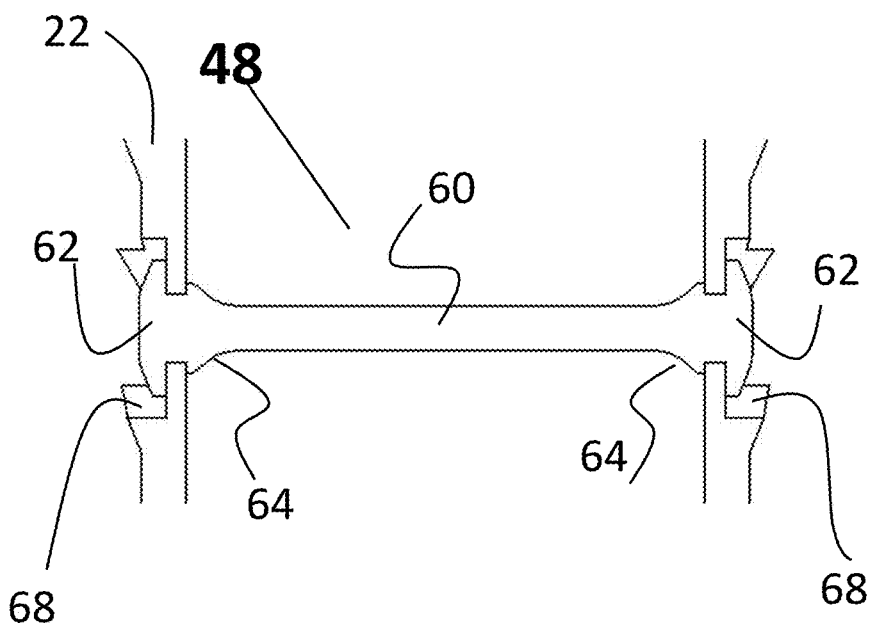
Figure 8C:
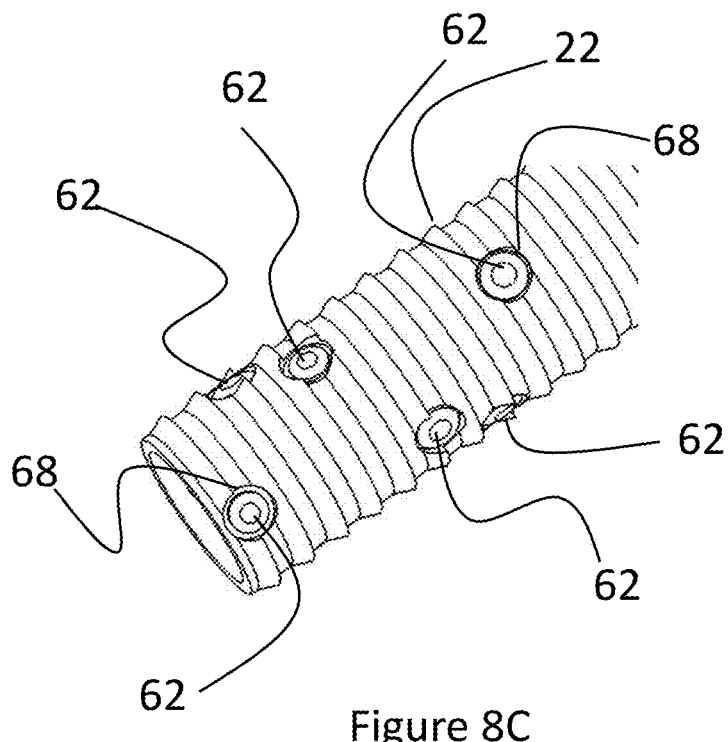

FIGS. 8A-8C demonstrate exemplary designs of the elastomeric band. FIG. 8A shows elastomeric band 48 having a main elastomeric band 60, comprising an externalbulges 62 and internal bulges 64. Bulges 62 and 64 are separated by grooves 66. In some embodiments, bulges 62 and 64 are configured to anchor elastomeric band 48 to the internal of cannula 22 body.

FIG. 8B shows how elastomeric band 48 is installed through two holes located at the sides of cannula 22 of surgical port 3. Each hole in cannula 22 is surrounded by a groove 68, also seen in FIG. 8C. Groove 68 holds and hides bulge 62 of elastomeric band 48. Elastomeric band 48 is anchored to cannula 22 throw a groove 66. Groove 66 is characterized by a width appropriate to fit to the thickness of cannula 22, enabling the anchoring of elastomeric band 48 to both sides of internal cannula body.

FIG. 8C presents an external view of cannula 22 of surgical port 1, bulges 62 of elastomeric band 48 are positioned in grooves 68, along cannula 22.

Figure 9A:
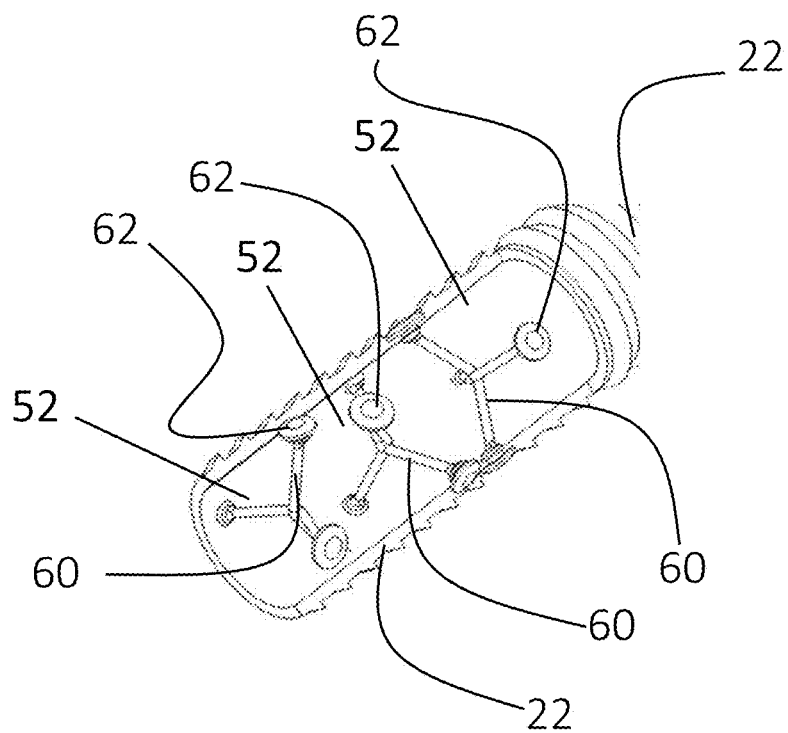
FIGS. 9A-9C are illustrations of an elastomeric band arrangement, according to some embodiments of the present invention.
Figure 9B:
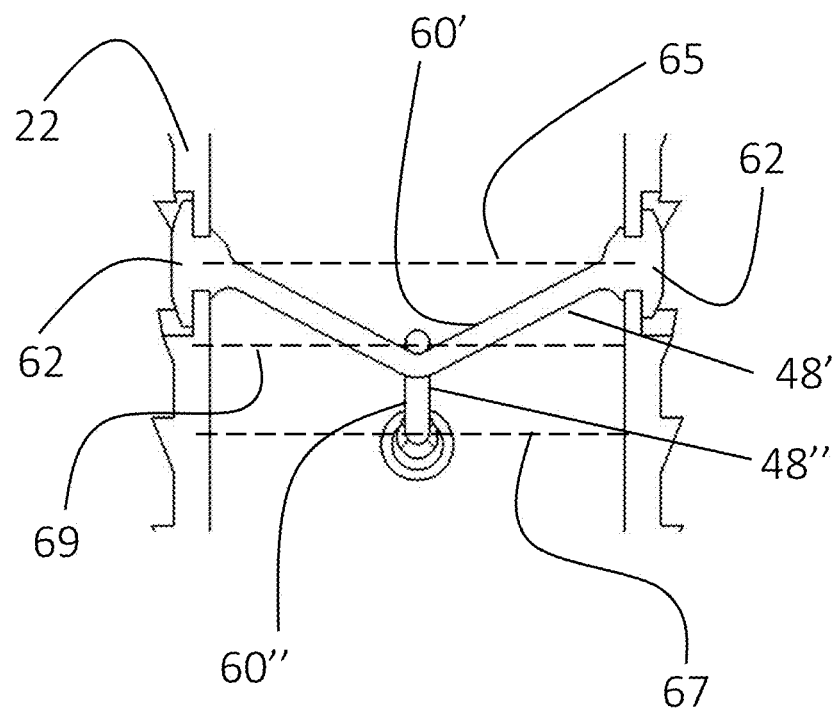
Figure 9C:
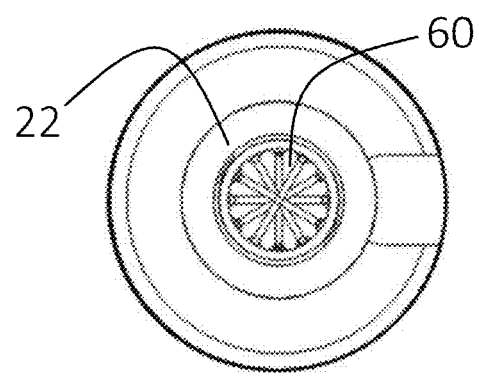

FIGS. 9A-9C illustrate elastomeric band arrangement according to some embodiments of the present invention in different views. Cannula 22 of the surgical port presented, comprises of three cleaning bands pairs 52 positioned along the long axis of cannula 22. As seen in FIG. 9B, each cleaning band is stretched between two holes that are positioned in a same plane, cleaning band 48' in plane 65 cleaning band 48' in plane 67. Both planes 65,67 are perpendicular to the long axis of cannula 22. String 60' is crossed over string 60" in a third plane 69 located between plane 65 and plane 67. In this arrangement, strings 60' 60" apply force on each other, while both strings may slide on each other, allowing the strings to adjust firmly to the lens surface of the endoscope, while the endoscope lens surface is pushed forward, and wipe it efficiently.

The initial force of each string 60, depends on the length of each band, the diameter of cannula 22 and the distances between planes 65 and 67 the angle between the bands, the material of the bands, the distance between the pairs, the location of each pair and the orientation of each pair of bands relative to the other pairs.

FIG. 9C illustrate the pattern of the three pairs of FIG. 9A as can be seen through the distal opening of cannula 22 of surgical port 1.

Figure 10A:
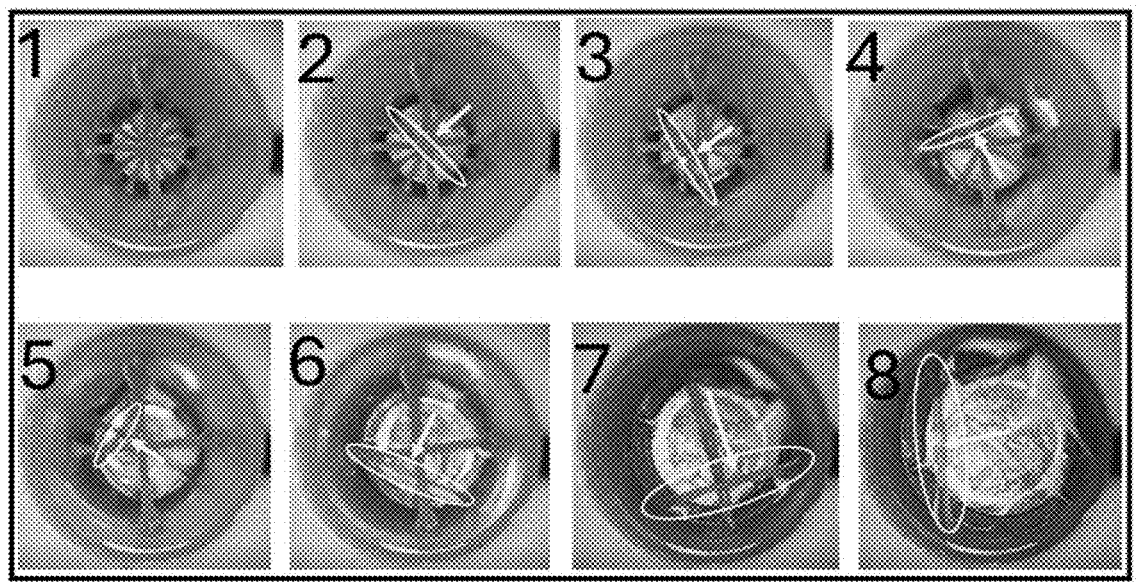
FIGS. 10A-10B present series of images taken from a video, recording of cleaning an endoscope lens, using the elastomeric bands pattern shown in FIGS. 9A-9C.
Figure 10B:
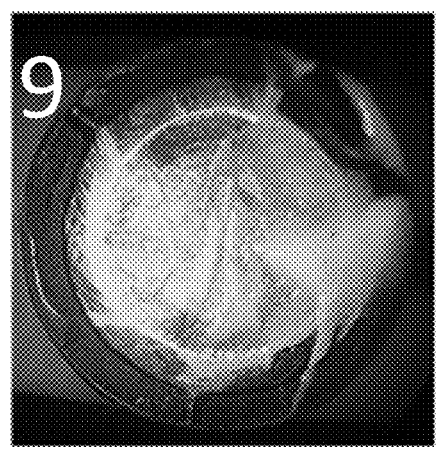

FIGS. 10A-10B illustrate wiping of 0° Endoscope using the surgical port of the invention. FIG. 10A presents a series of 8 images which were taken from a video recording a single pass of an endoscope through the surgical port of the invention. The surgical port comprises an elastomeric band pattern as shown in FIGS. 9A-9C. At each image, the active band is marked with ellipse and arrow indicates the direction of movement of the band. Image 1 shows endoscope lens approaching to the proximal pair of cleaning bands. Images 2-7 show endoscope lens pushes the cleaning bands from the center of the cannula to the sides of the cannula. A person skilled in the art would appreciate that the images show that the bands pass each in turn, over the lens surface, over overlapping areas, thus increasing the efficiency and quality of the wiping. FIG. 10B is a photo of the endoscopic lens after the endoscope lens was pushed through three pairs of cleaning bands. A person skilled in the art would appreciate that most of the lens was wiped after a single pass.

In some embodiments, the surgical port of the invention is designed to accommodate a typical obturator without compromising the at least one elastomeric band.

As used herein, the term "typical obturator" refers to an obturator comprising of a head, a shaft and a pointed head. An obturator is configured to facilitate the insertion of an endoscope into a body cavity or a passage.

As used herein, the term "modified obturator" refers to an obturator with a restructured body designed to improve functionality during procedures involving a trocar and cannula. Its body includes a socket that accommodates pairs of strings, ensuring they can surround the obturator without being subjected to friction force or pressure that might cause their tearing or distortion. The obturator's socket features slopes at both ends, allowing the strings to slide in and out smoothly and safely, while keeping the needed minimal gap between the outside diameter of the distal end of the obtirator and theinner diameter of the cannula to maintain a tight fit between the obturator distal end and the inner surface of the cannula, thus preventing tissue from getting jammed between the obturator and the inner surface of the cannula.

Figure 11A:
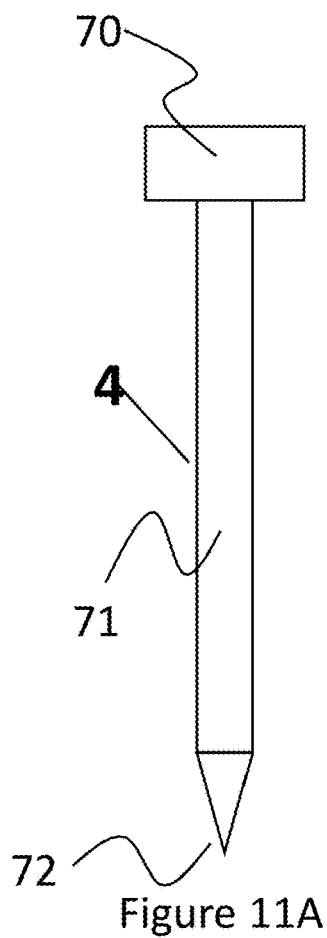
FIGS. 11A-11G are illustrations presenting (11A-11B) common obturator and (11C-11G) modified obturator according to some embodiments, of the present invention.
Figure 11B:
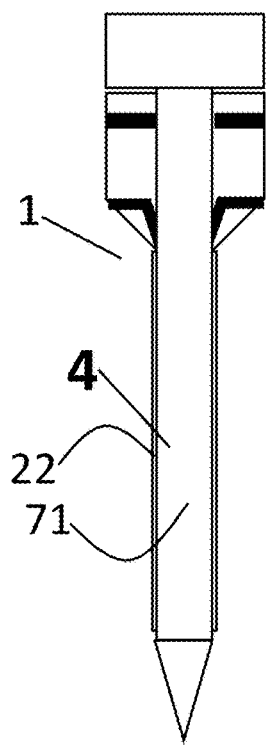

Reference is now made to FIG. 11A-11D illustrating a typical obturator and a modified obturator, solely or accommodated within the surgical port of the present invention. FIG. 11A-11B are illustration of a typical obturator and an obturator installed in a typical surgical port, respectively. A typical obturator 4 comprises head 70, shaft 71, and pointed head 72. Obturator 4 is configured to facilitate the insertion of an endoscope into a body cavity or passage. A person skilled in the art would appreciate that the obturator shaft 71 should be closely matched to the distal opening of cannula 22 to prevent a formation of a gap in which tissues can enter during procedure.

Figure 11C:
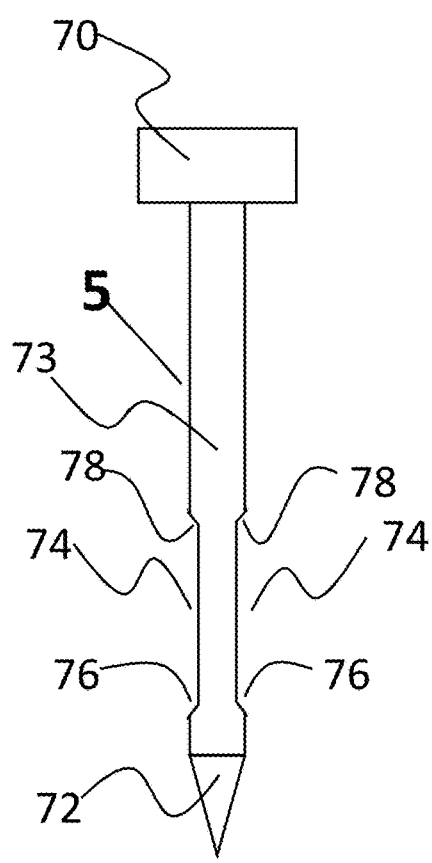
Figure 11D:
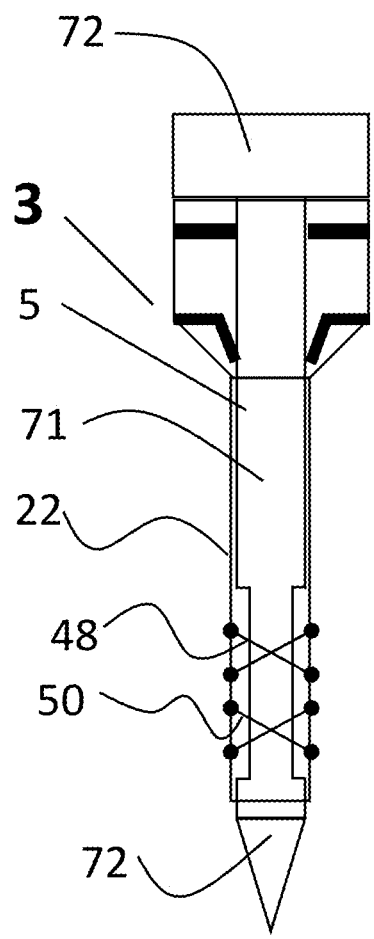

Reference is now made to FIG. 11C-11D illustrate a modified obturator according to some embodiments, of the present invention. Obturator 5 having a modified body 73. Body 73 comprises socket 74 that allows the pairs of strings 48 and 50 to surround the trocar body, without the trocar body stretching them or exerting pressure on them, this prevents string tearing or string distortion. Slopes 78 and 76 located at both ends of socket 74 allow strings 48 and 50 to slide into or out of socket 74 without risk of tearing. The distance between the distal end of socket 74 and the end of body 73 is as short as possible, while allowing a tight fit between the distal end of body 73 and the distal end of cannula 22, in order to prevent tissue jamming between the obturator body 73 and cannula 22.

Figure 11E:
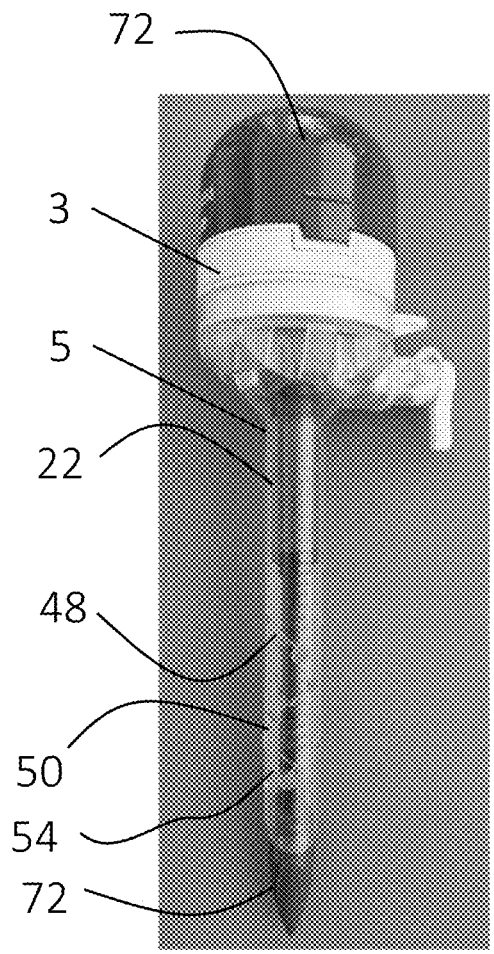
Figure 11F:
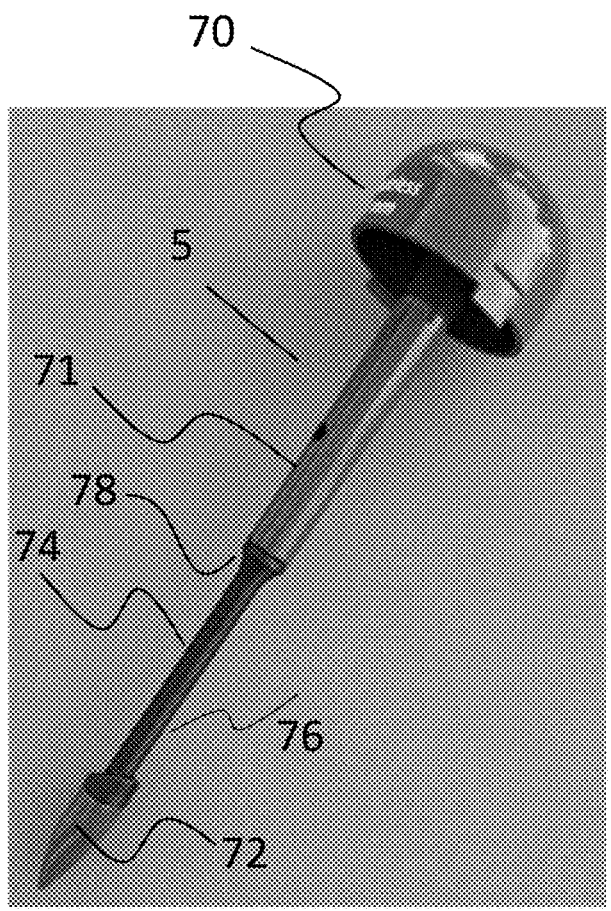
Figure 11G:
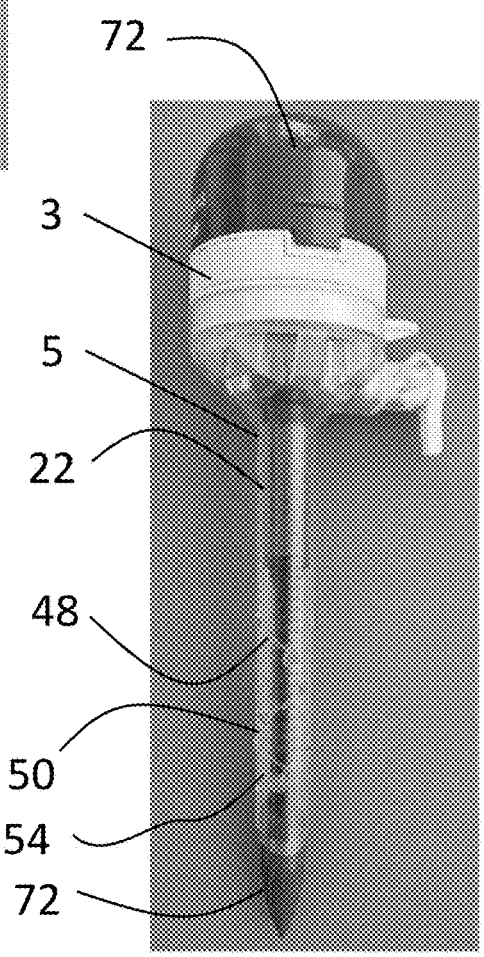

Reference is now made to FIG. 11E-11F are prototype photos of modified obturator 5. The prototype was tested in animal lab. During the operation modified obturator 5 no damage to the elastomeric bands was observed, and tissue did not stick between obturator body 71 and cannula 22 of the surgical port of the present invention.

In some embodiments, the modified obturator is designed to fit into a surgical port and facilitate its placement. A person skilled in the art would appreciate that the obturator must fit precisely to the distal opening of the cannula of the surgical port of the invention to prevent (i) inadequate sealing between the surgical port and surrounding tissues, (ii) tissue or organ damage, (iii) difficulty in insertion.

According to another aspect of the invention there is disclosed a method for cleaning surgical instruments within a body cavity comprising obtaining a surgical port having an at least one elastomeric band vertically to a longitudinal axis along a cannula interior body; and moving the surgical instrument over the at least one elastomeric band thereby obtaining a cleaned surgical instrument.

The present invention also discloses a system and methods thereof for adapting surgical port to integrate an at least one elastomeric band or a plurality of elastomeric bands into the lumen of the surgical port enabling the surgical port to serve also as a device for cleaning surgical tools operable in a body cavity, e.g., during a minimally invasive surgical procedure.

According to another aspect of the present invention, there is disclosed a modified obturator configured to allow the at least one elastomeric band to surround the obturator body while maintaining the integrity of the at least one elastomeric band. As used herein, the term "integrity" refers to the quality, performance, stability, strength, functionality, reliability or efficiency, including any combination thereof, of the elastomeric bands.

In some embodiments the modified obturator (5) comprises a head 70, a shaft 71, a pointed head 72 and a modified body 73 having a socket 74 enabling the at least one elastomeric band to surround a trocar body.

What is claimed is:

1. A surgical port for cleaning accommodated surgical instruments comprising
   a cannula and an at least one elastomeric band installed in said cannula, configured to clean said surgical instruments accommodated within;
   wherein said at least one elastomeric band is stretched from one side of cannula internal lumen wall to the other side of said cannula internal lumen wall of said surgical port; and said at least one elastomeric band crosses at least one other elastomeric band.

2. The surgical port of claim 1, wherein said at least one elastomeric band is placed vertically to a longitudinal axis along a cannula interior body.

3. The surgical port of claim 1, wherein at least two elastomeric bands are placed vertically to a longitudinal axis along a cannula interior body.

4. The surgical port of claim 1, wherein at least two elastomeric bands are placed in a same plane.

5. The surgical port of claim 1, wherein at least two elastomeric bands are placed on different planes.

6. The surgical port of claim 1, wherein said at least one elastomeric band ends are placed on different planes.

7. The surgical port of claim 6, wherein each end of each elastomeric band end is placed on different planes.

8. The surgical port of claim 1, wherein at least two of said at least one elastomeric band cross one another.

9. The surgical port of claim 1, wherein at least two of said at least one elastomeric band are arranged in a 3D grate pattern, a crossing pattern, and any combination thereof.

10. The surgical port of claim 1, wherein said at least one elastomeric band is immobilized to said cannula.

11. The surgical port of claim 1, wherein said at least one elastomeric band is made of rubber or silicone.

12. The surgical port of claim 1, further comprising holes to accommodate said at least one elastomeric band.

13. The surgical port of claim 12, wherein said holes are surrounded by grooves configured to protect said at least one elastomeric band.

14. The surgical port of claim 1, wherein typical obturator 4 or modified obturator 5 are configured to fit within said surgical port.

15. The surgical port of claim 14, wherein said modified obturator comprises head 70, shaft 71, a pointed head 72 and a modified body 73 having a socket 74, said modified obturator is configured to enable said at least one elastomeric band to surround the obturator body.

16. A method for cleaning surgical instruments within a body cavity comprising
obtaining a surgical port having an at least one elastomeric band vertically to a longitudinal axis along a cannula interior body; and
moving said surgical instrument over said at least one elastomeric band thereby obtaining a cleaned surgical instrument;
wherein said at least one elastomeric band is stretched from one side of cannula internal lumen wall to the other side of said cannula internal lumen wall of said surgical port; and said at least one elastomeric band crosses at least one other elastomeric band.

17. The method of claim 16, wherein at least two of said at least one elastomeric band cross one another.

18. The method of claim 16 wherein at least two of said at least one elastomeric band are arranged in a grate pattern, a crossing pattern, and any combination thereof.

19. The method of claim 16, wherein said at least one elastomeric band is made of rubber or silicone.

20. The method of claim 16, wherein said surgical port is either obtained by modifying a typical trocar 1 or by purchasing said surgical port.

* * * * *